[19] United States Patent
Sedelmeier et al.

[11] Patent Number: 5,693,807
[45] Date of Patent: Dec. 2, 1997

[54] SUBSTITUTED HYDROQUINONE DERIVATIVES

[75] Inventors: Gottfried Sedelmeier, Schallstadt; Gerhard Fischer, Bad Krozingen, both of Germany

[73] Assignee: Ciba-Geigy Corporation, Summit, N.J.

[21] Appl. No.: 465,628

[22] Filed: Jun. 5, 1995

Related U.S. Application Data

[62] Division of Ser. No. 154,641, Nov. 19, 1993, which is a division of Ser. No. 961,001, Oct. 14, 1992, Pat. No. 5,290,939.

[51] Int. Cl.$^6$ ................................................ C07D 211/32
[52] U.S. Cl. .................. 546/22; 546/184; 546/196; 546/245; 558/186; 558/187; 558/199; 568/9; 568/14; 568/16; 568/17; 568/644; 568/650; 568/655
[58] Field of Search ...................... 558/186, 187, 558/199; 568/9, 16, 17, 14, 644, 650, 655; 546/22, 184, 196, 245

[56] References Cited

U.S. PATENT DOCUMENTS

| | | | |
|---|---|---|---|
| 3,123,648 | 3/1964 | Wilkinson et al. | 260/612 |
| 4,210,655 | 7/1980 | Schenker et al. | 424/627 |
| 4,600,719 | 7/1986 | Schenker et al. | 514/320 |
| 4,829,067 | 5/1989 | Iijima et al. | 514/233.5 |
| 4,971,995 | 11/1990 | Schoofs et al. | 514/520 |
| 4,977,159 | 12/1990 | Sevrin et al. | 514/292 |
| 5,011,849 | 4/1991 | Gassner et al. | 514/365 |
| 5,290,939 | 3/1994 | Sedelmeier et al. | 546/196 |

FOREIGN PATENT DOCUMENTS

| | | | |
|---|---|---|---|
| 0302788 | 2/1989 | European Pat. Off. | C07D 47/04 |
| 405301836 | 3/1991 | Japan | C07C 43/23 |
| 1565055 | 4/1980 | United Kingdom . | |

OTHER PUBLICATIONS

Guillamel et al; J. Heterocyclic Chem. 27, 1047–1051 (1990), "Synthetic Routes to 2–(2–Benzofuranyl) benzoic Acids and their Cyclization into Benz [b] indeno [2 1–d] furan–10–ones".

Olah et al, "Synthetic Methods and Reactions; 77: Dimethyl Sulfoxide / Chlorosulfonyl Isocyanote: An Extremely Mild Reagent for Oxidation of Alcohol to Carbonyl Compounds" Synthesis 1980, pp. 141–142.

Guillaumel et al. "Recherches sur les derives nitres d' interet biologique" Eur. J. Chem. vol. 18: pp. 431–436 (1983).

Drugs of the Future vol. 10, pp. 371–373 (1985) "Brofaromine Hydrochloride".

Beilstein Handbuch Derorganischen Chemie–vol. 6. p. 1113 (1947).

Beilstein Handbuch–Der Organischen Chemie vol. 6, 2nd Supp. p. 1083 (1929).

Gueremy et al "3–(4 Piperidinyl alkyl) Indoles Selective Inhibitors of Neuronal 5–Hydroxy–tryptamine Uptake" J. Med. Chem vol. 23: 1306–1310 (1980).

Casiraghi et al. "Selective Reactions between Phenols and Formaldehyde A Superior Synthesis of Salicyl Alcohols" Synthesis pp. 124–125 (Feb. 1980).

Primary Examiner—Mukund J. Shah
Assistant Examiner—Sabiha Qazi
Attorney, Agent, or Firm—Gregory D. Ferraro

[57] ABSTRACT

The invention relates to substituted hydroquinone derivatives of the general formula I

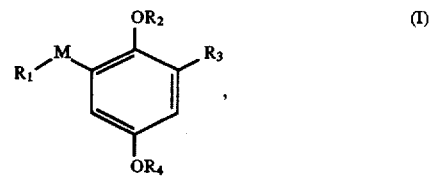

wherein $R_4$ is lower alkyl and either $R_1$ is hydroxy, halogen, a group of the formula $-P(=O)(R_5)R_6$ (Ia), a group of the formula $-P^+(R_7)(R_8)R_9 X^-$ (Ib) or a group of the formula $-Si(R_7)(R_8)R_9$ (Ic), M is methylene, $R_2$ is hydrogen or a group of the formula

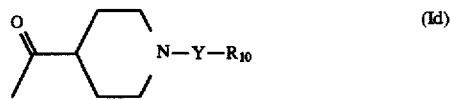

and $R_3$ is hydrogen or halogen, or $_1$ is hydroxy or lower alkoxy, M is carbonyl, $R_2$ is hydrogen and $R_3$ is halogen, each of $R_5$ and $R_6$, independently of the other, is lower alkyl, lower alkoxy Or N,N-di-lower alkylamino, or is benzyl, benzyloxy, phenyl or phenoxy, each of which is unsubstituted or mono- or di-substituted at the phenyl ring, to a process for the preparation of those compounds and to the use of those compounds, and to a process in which those compounds are used.

2 Claims, No Drawings

SUBSTITUTED HYDROQUINONE DERIVATIVES

This is a divisional of application Ser. No. 08/154,641 filed Nov. 19, 1993 which is a divisional of application Ser. No. 07/961,001 filed Oct. 14, 1992 now U.S. Pat. No. 5,290,939.

The invention relates to novel substituted hydroquinone derivatives of formula I

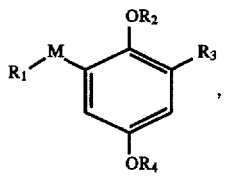

wherein $R_4$ is lower alkyl and either $R_1$ is hydroxy, halogen, a group of the formula —P(=O)($R_5$)$R_6$ (Ia), a group of the formula —P$^+$($R_7$)($R_8$)$R_9$X$^-$ (Ib) or a group of the formula —Si($R_7$)($R_8$)$R_9$ (Ic), M is methylene, $R_2$ is hydrogen or a group of the formula

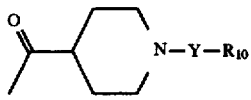

and $R_3$ is hydrogen or halogen, or $R_1$ is hydroxy or lower alkoxy, M is carbonyl, $R_2$ is hydrogen and $R_3$ is halogen, each of $R_5$ and $R_6$, independently of the other, is lower alkyl, lower alkoxy or N,N-di-lower alkylamino, or is benzyl, benzyloxy, phenyl or phenoxy, each of which is unsubstituted or mono- or di-substituted at the phenyl ring, wherein the substituents of the phenyl ring may be selected in each case from the group consisting of lower alkyl, lower alkoxy, nitro and halogen, each of $R_7$, $R_8$ and $R_9$, independently of the others, is lower alkyl, unsubstituted or mono- or di-substituted phenyl, wherein the substituents of the phenyl ring may be selected in each case from the group consisting of lower alkyl, lower alkoxy, nitro and halogen, or is furyl, X$^-$ is the anion of a hydrohalic acid, a lower alkanesulfonic acid, a halo-lower alkanesulfonic acid or of a benzenesulfonic acid that is unsubstituted or mono-substituted by lower alkyl or by halogen, and wherein either Y is a direct bond and $R_{10}$ is lower alkyl, allyl, cyano, lower alkanesulfonyl, halo-lower alkanesulfonyl, benzyl that is unsubstituted or mono- or di-substituted at the phenyl ring, wherein the substituents of the phenyl ring may be selected in each case from the group consisting of lower alkyl, lower alkoxy, nitro and halogen, or is benzenesulfonyl that is unsubstituted or mono-substituted by lower alkyl or by halogen, or Y is a group of the formula —(C=O)— (Ie) or a group of the formula —(C=S)— (If) and $R_{10}$ is halogen, lower alkyl, halo-lower alkyl, lower alkoxy, lower alkenyloxy, phenyl-lower alkenyloxy, halo-lower alkoxy or lower alkylthio, or is phenyl, phenoxy, phenylthio, benzyl, benzyloxy or benzylthio, each of which is unsubstituted or mono- or di-substituted at the phonyl ring, wherein the substituents of the phenyl ring may be selected in each case from the group consisting of lower alkyl, lower alkoxy, nitro and halogen, with the proviso that, in a compound I wherein $R_1$ is a group Ib wherein each of $R_7$, $R_8$ and $R_9$ is unsubstituted phenyl and X$^-$ is the bromide ion, M is methylene, $R_2$ is hydrogen and $R_4$ is methyl, $R_3$ is other than hydrogen, and with the further proviso that, in a compound I wherein $R_1$ is hydroxy, M is methylene, $R_2$ is hydrogen and $R_4$ is methyl or ethyl, $R_3$ is other than hydrogen, in free form or in salt form, to a process for the preparation of those compounds and to the use of those compounds, and to a process in which those compounds are used.

Compounds I in salt form are especially corresponding acid addition salts (of compounds I having at least one basic centre) and corresponding salts with bases (of compounds I having at least one acidic centre), preferably corresponding pharmaceutically acceptable salts. The acid addition salts are formed, for example, with strong inorganic acids, such as mineral acids, for example sulfuric acid, a phosphoric acid or a hydrohalic acid, with strong organic carboxylic acids, such as lower alkanecarboxylic acids, for example acetic acid, unsaturated or saturated dicarboxylic acids, for example oxalic, malonic, succinic, maleic, fumaric, phthalic or terephthalic acid, hydroxycarboxylic acids, for example ascorbic, glycolic, lactic, malic, tartaric or citric acid, amino acids, for example aspartic or glutamic acid, or benzoic acid, or with organic sulfonic acids, such as lower alkane-sulfonic or unsubstituted or substituted benzenesulfonic acids, for example methane- or p-toluene-sulfonic acid. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propyl-amine, or a mono-, di- or tri-hydroxy-lower alkylamine, for example mono-, di- or tri-ethanolamine. The compounds I may also be in the form of internal salts, for example when $R_1$ is a group Ib. Also included are salts that are unsuitable for pharmaceutical uses, which can be used, for example, for the isolation and/or purification of free compounds I and their pharmaceutically acceptable salts. In view of the close relationship between the compounds I in free form and in the form of their salts, hereinbefore and hereinafter any reference to the free compounds I or their salts should be understood as including the corresponding salts or free compounds I, respectively, as appropriate and expedient.

Unless otherwise defined, the general terms used hereinbefore and hereinafter have the definitions given below.

Unless otherwise deemed, radicals and compounds designated "lower" are to be understood as being radicals and compounds containing up to and including 7, especially up to and including 4, carbon atoms.

Lower alkyl is $C_1$–$C_4$alkyl, i.e. methyl, ethyl, propyl, isopropyl, butyl, isobutyl, sec-butyl or tert-butyl, and includes also $C_5$–$C_7$alkyl radicals, i.e. corresponding pentyl, hexyl and heptyl radicals.

Lower alkoxy is $C_1$–$C_4$alkoxy, i.e. methoxy, ethoxy, propoxy, isopropoxy, butoxy, isobutoxy, sec-butoxy or tert-butoxy, and includes also $C_5$–$C_7$alkoxy radicals, i.e. corresponding pentyloxy, hexyloxy and heptyloxy radicals.

Lower alkenyloxy is, for example, allyloxy; phenyl-lower alkenyloxy is, for example, 3-phenylprop-2-enyl.

Lower alkylthio is $C_1$–$C_4$alkylthio, i.e. methylthio, ethylthio, propylthio, isopropylthio, butylthio, isobutylthio, sec-butylthio or tert-butylthio, and includes also $C_5$–$C_7$alkylthio radicals, i.e. corresponding pentylthio, hexylthio and heptylthio radicals.

Halogen is especially chlorine or bromine, also fluorine or iodine.

N,N-di-lower alkylamino is N,N-di-lower alkylamino wherein the two N-lower alkyl radicals are identical or different and are each as deemed above in the definition of lower alkyl, such as N,N-dimethylamino, N,N-diethylamino, N,N-diisopropylamino, N-butyl-N-methylamino, N,N-dipentylamino or N-pentyl-N-methylamino.

Halo-lower alkyl—as compared with lower alkyl—contains one, two or three identical or different halogen atoms at one of its carbon atoms instead of hydrogen atoms and is halo-lower alkyl wherein lower alkyl is as defined above in the definition of lower alkyl and halogen is as defined above in the definition of halogen, such as trifluoromethyl, trichloromethyl, 2,2,2-trifluoroethyl or 3,3,3-trifluoropropyl.

Halo-lower alkoxy—as compared with lower alkoxy—contains one, two or three identical or different halogen atoms at one of its carbon atoms instead of hydrogen atoms and is halo-lower alkoxy wherein lower alkoxy is as defined above in the definition of lower alkoxy and halogen is as defined above in the definition of halogen, such as trifluoromethoxy, trichloromethoxy, 2-iodoethoxy, 2,2,2-trifluoroethoxy or 3,3,3-trifloropropoxy.

Lower alkanesulfonyl is $C_1$–$C_4$alkanesulfonyl, such as methanesulfonyl, ethanesulfonyl, propanesulfonyl, butanesulfonyl or tert-butanesulfonyl, and includes also $C_5$–$C_7$alkanesulfonyl radicals, i.e. corresponding pentanesulfonyl, hexanesulfonyl and heptanesulfonyl radicals.

Halo-lower alkanesulfonyl—as compared with lower alkanesulfonyl—contains one, two or three identical or different halogen atoms at one of its carbon atoms instead of hydrogen atoms and is halo-lower alkanesulfonyl wherein lower alkanesulfonyl is as defined above in the definition of lower alkanesulfonyl and halogen is as defined above in the definition of halogen, such as trifluoromethanesulfonyl, trichloromethanesulfonyl, 2,2,2-trifluoroethanesulfonyl or 3,3,3-trifluoropropanesulfonyl.

Anions of a hydrohalic acid (halide ions) are especially the chloride and the bromide ion, also the fluoride ion and the iodide ion.

Anions of a lower alkanesulfonic acid (lower alkanesulfonate ions) are anions wherein the lower alkanesulfonyl on which their lower alkanesulfonate structure is based is as defined above in the definition of lower alkanesulfonyl, such as the methanesulfonate ion, the ethanesulfonate ion, the propanesulfonate ion, the butanesulfonate ion or the tert-butanesulfonate ion.

Anions of a halo-lower alkanesulfonic acid (halo-lower alkanesulfonate ions)—as compared with anions of a lower alkanesulfonic acid (lower alkanesulfonate ions)—contain one, two or three identical or different halogen atoms at one of their carbon atoms instead of hydrogen atoms and are anions wherein the lower alkanesulfonyl on which their lower alkanesulfonate partial structure is based is as defined above in the definition of lower alkanesulfonyl and halogen is as defined above in the definition of halogen, such as the trifluoromethanesulfonate ion, the trichloromethanesulfonate ion, the 2,2,2-trifluoroethanesulfonate ion or the 3,3,3-trifluoropropanesulfonate ion.

Anions of a benzenesulfonic acid that is unsubstituted or mono-substituted by lower alkyl or by halogen (benzenesulfonate ions that are unsubstituted or mono-substituted by lower alkyl or by halogen) are anions wherein lower alkyl is as defined above in the definition of lower alkyl and halogen is as defined above in the definition of halogen, such as the benzenesulfonate ion, the p-toluenesulfonate ion or the p-chlorobenzenesulfonate ion.

Preference is given within the scope of the invention to compounds of formula I wherein $R_4$ is lower alkyl and either $R_1$ is hydroxy, halogen, a group Ia or a group Ib, M is methylene, $R_2$ is hydrogen or a group Id and $R_3$ is hydrogen or halogen, or $R_1$ is hydroxy or lower alkoxy, M is carbonyl, $R_2$ is hydrogen and $R_3$ is halogen, each of $R_5$ and $R_6$, independently of the other, is lower alkoxy, each of $R_7$, $R_8$ and $R_9$ is unsubstituted phenyl or furyl, $X^-$ is the anion of a hydrohalic acid, Y is a group Ie and $R_{10}$ is lower alkoxy, lower alkenyloxy or phenyl-lower alkenyloxy, with the proviso that, in a compound I wherein R1 is a group Ib wherein $X^-$ is the bromide ion, M is methylene, $R_2$ is hydrogen and $R_4$ is methyl, $R_3$ is other than hydrogen, and with the further proviso that, in a compound I wherein $R_1$ is hydroxy, M is methylene, $R_2$ is hydrogen and $R_4$ is methyl or ethyl, $R_3$ is other than hydrogen, in free form or in salt form.

Special preference is given within the scope of the invention to compounds of formula I wherein $R_1$ is hydroxy or a group Ib, M is methylene, $R_2$ is hydrogen or a group Id, $R_3$ is hydrogen or halogen, $R_4$ is lower alkyl, each of $R_7$, $R_8$ and $R_9$ is unsubstituted phenyl, $X^-$ is the anion of a hydrohalic acid, Y is a group Ie and $R_{10}$ is lower alkoxy, with the proviso that, in a compound I wherein R1 is a group Ib wherein $X^-$ is the bromide ion, M is methylene, $R_2$ is hydrogen and $R_4$ is methyl, $R_3$ is other than hydrogen, and with the further proviso that, in a compound I wherein $R_1$ is hydroxy, M is methylene, $R_2$ is hydrogen and $R_4$ is methyl or ethyl, $R_3$ is other than hydrogen, in free form or in salt form.

More especial preference is given within the scope of the invention to compounds of formula I wherein $R_1$ is hydroxy or a group Ib, M is methylene, $R_2$ is hydrogen or a group Id, $R_3$ is halogen, such as bromine, $R_4$ is $C_1$–$C_4$alkyl, such as methyl, each of $R_7$, $R_8$ and $R_9$ is unsubstituted phenyl, $X^-$ is the anion of a hydrohalic acid, such as the chloride ion or the bromide ion, Y is a group Ie and $R_{10}$ is $C_1$–$C_4$alkoxy, such as ethoxy, in free form or in salt form.

Very special preference is given within the scope of the invention to compounds of formula I wherein $R_1$ is a group Ib, M is methylene, $R_2$ is hydrogen or a group Id, $R_3$ is halogen, such as bromine, $R_4$ is $C_1$–$C_4$alkyl, such as methyl, each of $R_7$, $R_8$ and $R_9$ is unsubstituted phenyl, $X^-$ is the anion of a hydrohalic acid, such as the chloride ion or the bromide ion, Y is a group Ie and $R_{10}$ is $C_1$–$C_4$alkoxy, such as ethoxy, in free form or in salt form.

Most especially preferred within the scope of the invention are compounds of formula I wherein $R_1$ is a group Ib, M is methylene, $R_2$ is hydrogen, $R_3$ is halogen, such as bromine, $R_4$ is $C_1$–$C_4$alkyl, such as methyl, each of $R_7$, $R_8$ and $R_9$ is unsubstituted phenyl and $X^-$ is the anion of a hydrohalic acid, such as the chloride ion or the bromide ion, in free form or in salt form.

Within the scope of the invention, preference is given specifically to the compounds of formula I, in free form or in salt form, that are mentioned in the Examples.

The invention relates also to the process for the preparation of the compounds of formula I, in free form or in salt form, wherein a) for the preparation of a compound of formula I wherein $R_1$ is hydroxy or lower alkoxy, M is carbonyl, $R_2$ is hydrogen and $R_3$ is halogen and $R_4$ is lower alkyl, or $R_1$ is a group of the formula —$P^+(R_7)(R_8)R_9X^-$ (Ib), M is methylene, $R_2$ is hydrogen, $R_3$ is hydrogen, $R_4$ is methyl, $R_7$, $R_8$ and $R_9$ are unsubstituted phenyl and $X^-$ is bromide, or of a salt thereof, a compound of the formula

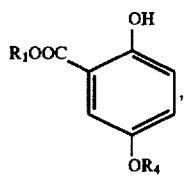

(II)

wherein $R_1$, $R_2$ and $R_4$ are as defined, or a salt thereof, is halogenated in the m-position with respect to the $R_1$—C(=O)— group and/or b) for the preparation of a compound of formula I wherein $R_1$ is hydroxy, M is methylene, $R_2$ is hydrogen, $R_3$ is hydrogen or halogen and $R_4$ is lower alkyl, with the proviso that $R_3$ is other than hydrogen when $R_4$ is methyl or ethyl, or of a salt thereof, a compound of the formula

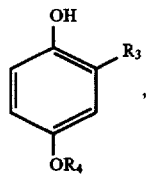

(III)

wherein $R_3$ is hydrogen or halogen and $R_4$ is lower alkyl, or a salt thereof is reacted with paraformaldehyde or trioxane, or in a compound of the formula

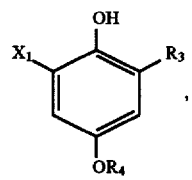

(IV)

wherein $X_1$ is the formyl group, carboxy or lower alkoxycarbonyl, $R_3$ is halogen and $R_4$ is lower alkyl, or in a salt thereof, the group $X_1$ is reduced to hydroxymethyl and/or c) for the preparation of a compound of formula I wherein $R_1$ is halogen, M is methylene, $R_2$ is hydrogen and $R_3$ is hydrogen or halogen, or of a salt thereof, in a compound of the formula

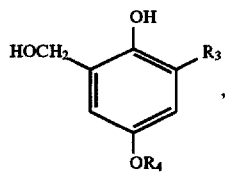

(V)

the hydroxymethyl group is converted into halomethyl, or a compound of the formula

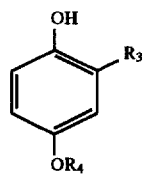

(III)

is reacted with paraformaldehyde or trioxane and a hydrohalic acid and/or d) for the preparation of a compound of formula I wherein $R_1$ is a group of the formula —P(=O)($R_5$)$R_6$(Ia), a group of the formula —P$^+$($R_7$)($R_8$)$R_9$X$^-$ (Ib) or a group of the formula —Si($R_7$)($R_8$)$R_9$(Ic), M is methylene, $R_2$ is hydrogen, $R_3$ is hydrogen or halogen and $R_4$ is lower alkyl and $R_5$, $R_6$, $R_7$, $R_8$, $R_9$ and X$^-$ are as defined for formula I, with the proviso that $R_3$ is other than hydrogen when $R_1$ is a group (Ib), $R_4$ is methyl, $R_7$, $R_8$ and $R_9$ are unsubstituted phenyl and X$^-$ is bromide, or of a salt thereof, a compound of the formula

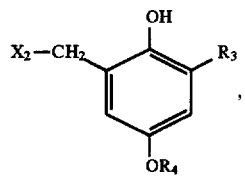

(VI)

wherein $X_2$ is halogen, $R_3$ is hydrogen or halogen and $R_4$ is lower alkyl, is reacted with a compound of the formula VIIa, VIIb or VIIc

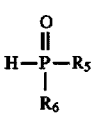

(VIIa)

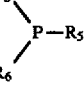

(VIIb)

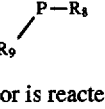

(VIIc)

or with a salt thereof, or is reacted first with magnesium and then with a compound of the formula

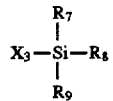

(VIId)

wherein $R_5$, $R_6$, $R_7$, $R_8$ and $R_9$ are as defined for formula I and $X_3$ is halogen and/or e) for the preparation of a compound of formula I wherein $R_1$ is a group of the formula —P(=O)($R_5$)$R_6$(Ia), a group of the formula —P$^+$($R_7$)($R_8$)$R_9$X$^-$(Ib) or a group of the formula —Si($R_7$)($R_8$)$R_9$(Ic), M is methylene, $R_2$ is hydrogen, $R_3$ is halogen and $R_4$ is lower alkyl and $R_5$, $R_6$, $R_7$, $R_8$, $R_9$ and X$^-$ are as defined for formula I, or of a salt thereof, a compound of the formula

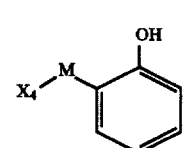

(VIII)

wherein $X_4$ is a group of the formula —P(=O)($R_5$)$R_6$(Ia), a group of the formula —P$^+$($R_7$)($R_8$)$R_9$X$^-$(Ib) or a group of the formula —Si($R_7$)($R_8$)$R_9$(Ic), M is methylene and $R_4$ is lower alkyl, is halogenated in the m-position with respect to the $R_1$-M group and/or f) for the preparation of a compound of formula I wherein $R_1$ is a group of the formula —P(=O)($R_5$)$R_6$(Ia), a group of the formula —P$^+$($R_7$)($R_8$)$R_9$X$^-$(Ib) or a group of the formula —Si($R_7$)($R_8$)$R_9$(Ic), M is methylene, $R_2$ is a group of the formula

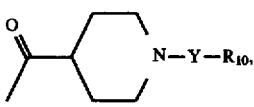

(Id)

$R_3$ is hydrogen or halogen and $R_4$ is lower alkyl and $R_5$, $R_6$, $R_7$, $R_8$, $R_9$, $R_{10}$, Y and $X^-$ are as defined for formula I, or of a salt thereof, a compound of the formula

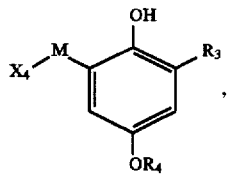

(IX)

wherein $X_4$ is a group of the formula $-P(=O)(R_5)R_6$ (Ia), a group of the formula $-P^+(R_7)(R_8)R_9X^-$ (Ib) or a group of the formula $-Si(R_7)(R_8)R_9$ (Ic), M is methylene, $R_3$ is hydrogen or halogen and $R_4$ is lower alkyl, and $R_5$, $R_6$, $R_7$, $R_8$, $R_9$ and $X^-$ are as defined for formula I, is reacted with a compound of the formula

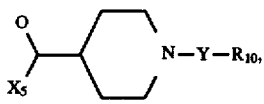

(X)

or with a salt thereof, wherein $X_5$ is halogen or a group of the formula $X_7$—O—, wherein $X_7$ denotes lower alkanesulfonyl, lower alkoxycarbonyloxy, or lower alkanoyl or a group of the formula

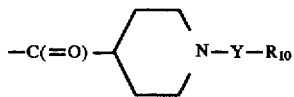

(Xa)

and $R_{10}$ and Y are as defined for formula I, and if desired a resulting compound is converted into a different compound of formula I, a mixture of isomers obtainable in accordance with the process is separated into its components and the preferred isomer in each case is isolated, and/or a free compound obtainable in accordance with the process is converted into a salt or a salt obtainable in accordance with the process is converted into the corresponding free compound.

The reactions of the process and the preparation of novel starting materials and intermediates are carried out analogously to the methods of reacting and forming known starting materials and intermediates. In those reactions, even when not expressly mentioned below, the auxiliaries, such as the catalysts, the condensation agents and the solvolysis agents and/or the solvents and diluents, and the reaction conditions, such as the temperature and pressure conditions, and, where appropriate, the protective gases, that are customary in each case are used.

The halogenation of compounds of formula II in accordance with Process step a) is effected, for example, by reaction with elementary halogen, especially bromine, advantageously in an organic solvent, for example in an aliphatic alcohol, especially a lower alkanol, such as methanol, ethanol, propanol or isopropanol. The halogenation is preferably carried out at normal or slightly reduced temperature, for example in a temperature range of from approximately 0° to approximately 30° C., especially from approximately 0° to approximately 20° C. When carboxylic acids II are used as starting materials, the carboxy group is at the same time esterified in the desired manner to form the corresponding lower alkoxycarbonyl group.

The starting materials for Process step a) are known.

The reaction of compounds of formula III with paraformaldehyde or trioxane in accordance with Process step b) is effected, for example, in the presence of an acidic condensation agent, such as a weak Lewis acid, especially anhydrous boric acid. The acid is preferably produced in situ by azeotropic distillation with a solvent that forms an azeotropic mixture with water, for example with toluene. The reaction is preferably carried out at elevated temperature, for example in a temperature range of from approximately 60° to approximately 120° C., especially from approximately 80° to approximately 100° C.

The reduction of formyl, carboxy and lower alkoxycarbonyl $X_1$ in compounds of formula IV is effected preferably by reaction with a di-light metal hydride, for example with lithium aluminium hydride or especially sodium borohydride. The reaction is preferably carried out in an ethereal solvent, such as an aliphatic or cycloaliphatic ether, for example in diethyl ether, methoxybutane, tetrahydrofuran or dioxane, or, when sodium borohydride is used, in an aliphatic alcohol, such as a lower alkanol, for example in methanol or ethanol, at normal or, advantageously, slightly reduced temperature, for example in a temperature range of from approximately 0° to approximately 40° C., especially from approximately 5° to approximately 20° C.

Starting materials of formula III and also compounds of formula IV wherein $X_1$ is formyl are known; starting materials of formula IV wherein $X_1$ is carboxy or lower alkoxycarbonyl are preferably prepared in accordance with Process step a).

The conversion of hydroxymethyl into halomethyl in accordance with Process step c) is effected in customary manner, for example by reaction with a hydrohalic acid, such as hydrogen chloride or especially hydrogen bromide, or with a compound that yields hydrogen halide. Suitable examples are ammonium halides, such as ammonium bromide or, with a view to the further use in Process step d), especially phosphonium halides, such as compounds of the formula $HP+(R_7)(R_8)R_9X-$. The reaction is advantageously carried out in an organic solvent, such as an aliphatic carboxylic acid or a lower alkyl ester or nitrile derived therefrom, for example in acetic acid, ethyl acetate or acetonitrile. The choice of solvent is not, however, critical; for example toluene or benzene may also be used.

Starting materials of formula V wherein $R_3$ is hydrogen and $R_4$ is methyl or ethyl are known; other compounds of formula V can be prepared, for example, in accordance with Process step b).

The reaction of intermediates of formula VI with compounds of formula VIIa, VIIb or VIIc in accordance with Process step d) is carried out in customary manner. For example, the reaction of compounds of formula VI with compounds of formula VII or VIIb is preferably carried out at elevated temperature, for example in a temperature range of from approximately 100° to approximately 200° C., preferably from approximately 120° to approximately 140° C. (Michaelis-Arbusow method).

The reaction of compounds of formula VI with compounds of formula VIIc is preferably carried out in the presence of an organic solvent or diluent, such as a lower alkane-carboxylic acid ester or lower alkanecarboxylic acid nitrile, such as ethyl acetate or acetonitrile, if necessary with heating, for example in a temperature range of from approximately 30° to approximately 100° C., preferably from approximately 40° to approximately 80° C.

In a preferred embodiment in which Process steps c) and d) are combined, the intermediate of formula VI is advantageously prepared in situ from the corresponding compound of formula V by treatment with a hydrohalic acid, for example hydrogen chloride, or by using the compound of formula VIIc in the form of a hydrogen halide salt, and is reacted further without being isolated.

The introduction of the group of formula Ic by reacting compounds of formula VI first with magnesium and then with a compound of formula VIId is effected preferably in an ethereal solvent, such as a di-lower alkyl ether or lower alkylene ether, such as diethyl ether, methoxybutane or tetrahydrofuran, if necessary with cooling, for example in a temperature range of from approximately −25° C. to room temperature, especially from approximately 0° to approximately 20° C.

The halogenation of compounds of formula VIII in accordance with Process step e) is effected, for example, by reaction with elementary halogen, especially bromine, advantageously in an organic solvent, for example in an aliphatic alcohol, especially a lower alkanol, such as methanol, ethanol, propanol or isopropanol.

Starting materials of formula VIII wherein $X_4$ is a group of formula Ic, M is methylene, $R_7$, $R_8$ and $R_9$ are unsubstituted phenyl, $X^-$ is bromide and $R_4$ is methyl are known; other compounds of formula VIII can be prepared, for example, in accordance with Process step d) or c)+d).

The reaction of compounds of formulae IX and X in accordance with Process step f) is effected preferably in the presence of a basic condensation agent, such as an organic nitrogen base, such as an aromatic nitrogen base, for example pyridine or quinoline, or an aliphatic amine, especially a tri-lower alkylamine, such as triethylamine, advantageously in an organic solvent, for example in a lower alkanecarboxylic acid ester or lower alkane-carboxylic acid nitrile, such as ethyl acetate or acetonitrile, if necessary with heating, for example in a temperature range of from approximately 25° to approximately 100° C., preferably from approximately 40° to approximately 80° C. $X_5$ as halogen is especially chlorine or bromine, as lower alkanesulfonyloxy is especially methanesulfonyloxy and as lower alkoxycarbonyloxy is especially ethoxy- or tert.-butyloxycarbonyloxy.

Compounds obtainable in accordance with the process can be convened in customary manner into different compounds of formula I.

Resulting salts can be convened into the free compounds in a manner known per se, for example by treatment with a base, such as an alkali metal hydroxide, a metal carbonate or hydrogen carbonate, or ammonia, or with a different salt-forming base mentioned at the beginning, or with an acid, such as a mineral acid, for example hydrochloric acid, or with a different salt-forming acid mentioned at the beginning.

Resulting salts can be converted into different salts in a manner known per se, acid addition salts, for example, by treatment with a suitable metal salt, such as a sodium, barium or silver salt, of a different acid in a suitable solvent in which an inorganic salt that is being formed is insoluble and therefore does not participate in the reaction equilibrium, and base salts by freeing the free acid and converting it into a salt again.

The compounds of formula I, including their salts, may also be obtained in the form of hydrates or may include the solvent used for crystallisation.

In view of the close relationship between the novel compounds in free form and in the form of their salts, hereinbefore and hereinafter any reference to the free compounds or their salts should be understood as including the corresponding salts or free compounds, respectively, as appropriate and expedient.

Resulting mixtures of diastereomers and mixtures of racemates can be separated into the pure diastereomers and racemates on the basis of the physical and chemical differences between their constituents in known manner, for example by chromatography and/or fractional crystallisation.

Resulting racemates can also be separated into the optical antipodes by known methods, for example by recrystallisation from an optically active solvent, with the aid of microorganisms, or by converting the resulting mixture of diastereomers or racemate with an optically active auxiliary compound, for example according to the acidic, basic or functionally modifiable groups contained in compounds of formula I with an optically active acid or base or an optically active alcohol, into mixtures of diastereomeric salts or functional derivatives, such as esters, and separating the latter into the diastereomers from which the particular enantiomer desired can be freed in the customary manner. Suitable bases, acids and alcohols for that purpose are, for example, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as cinchonic acid or B- or L-tartaric acid, D- or L-di-o-toluyltartaric acid, D- or L-malic acid, B- or L-mandelic acid, or D- or L-camphorsulfonic acid, and optically active alcohols, such as borneol or L- or L-(1-phenyl)ethanol.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds of the invention, especially to those starting materials resulting in the compounds of formula I that were described at the beginning as being preferred, to processes for the preparation thereof and to their use as intermediates.

The compounds of formula I, including those wherein $R_1$ is a group Ib wherein each of $R_7$, $R_8$ and $R_9$, independently of the others, is unsubstituted phenyl and $X^-$ is the bromide ion, M is methylene, $R_2$ is hydrogen, $R_4$ is methyl and $R_3$ is hydrogen, can be used for the preparation of compounds of the formula

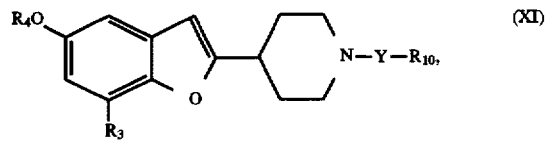

wherein $R_3$, $R_4$, $R_{10}$ and Y are as defined. Those compounds are valuable intermediates for the preparation of corresponding anti-depressively active compounds of the formula

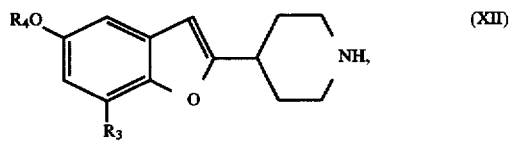

especially brofaromine ($R_3$=Br; $R_4$=CH$_3$), into which they can be converted in known manner by removal of the group of the formula —Y—$R_{10}$.

The conventional process for the preparation of brofaromine comprises a complicated 8-step synthesis corresponding to the following reaction scheme A1–A8 and uses as starting material 5-methoxysalicylaldehyde, which has to be prepared in advance by formylating 4-methoxyphenol in accordance with Reimer-Tiemann (A1) and is then brominated (A2). The resulting 3-bromo-5-methoxy-salicylaldehyde is then condensed with 4-chloromethylpyridine (A3). The resulting 4-(7-bromo-5-methoxy-benzofuran-2-yl)-pyridine is N-methylated to form the N-methylpyridinium salt (A4), is reduced with sodium boranate to form N-methyl-1,2,5,6-tetrahydropyridine (A5) and hydrogenated to form 1-methyl-4-(7-bromo-5-methoxy-benzofuran-2-yl)piperidine (A6). The last-mentioned compound is then demethylated by reaction with a haloformic acid ester with the formation of the corresponding 4-(7-bromo-5-methoxy-benzofuran-2-yl)piperidine-1-carboxylic acid ester (A7), which, finally, is cleaved to form brofaromine (A8).

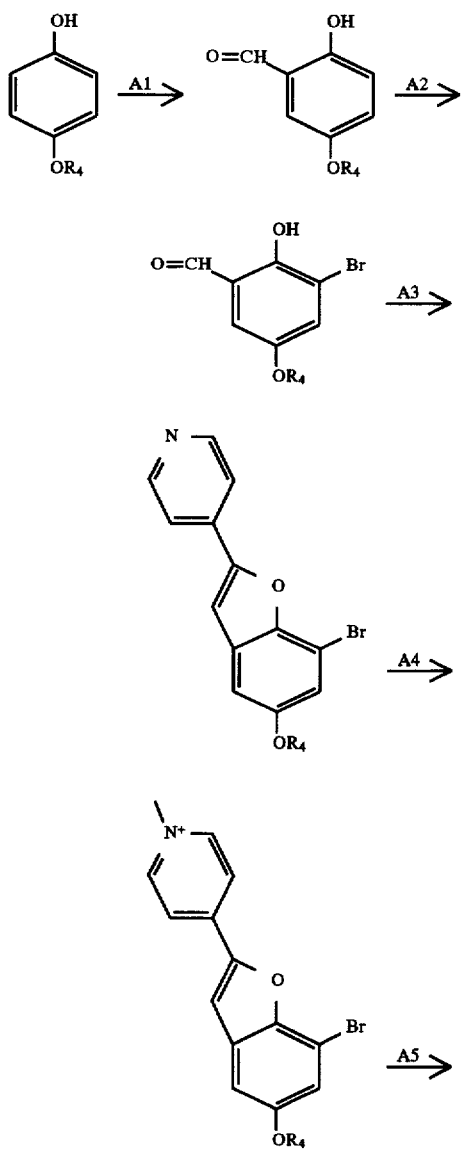

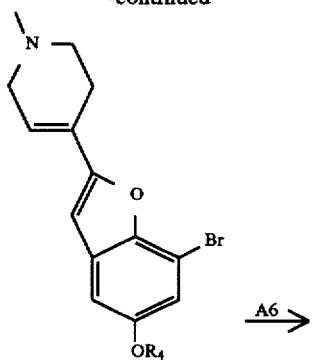

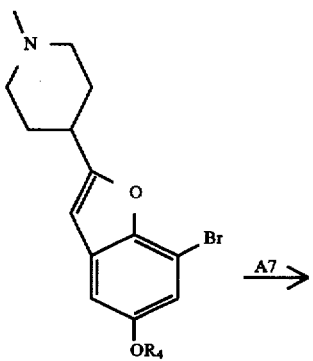

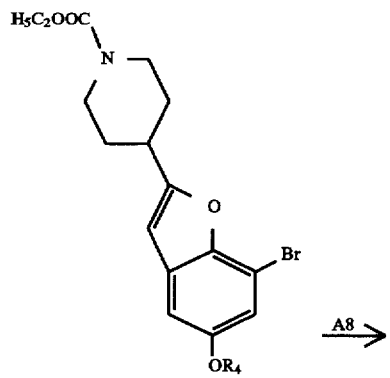

That process has decided disadvantages. In particular, using 4-methoxyphenol as starting material, a maximum total yield of brofaromine of only 12.7% of the theoretical yield is obtained. Steps A1 and A2, which lead to 3-bromo-5-methoxy-salicylaldehyde, are high-loss steps and are difficult to control from a technical point of view (yield 45% of the theoretical yield).

Owing to the large number of process steps and the disadvantageous fact that at step A6 up to 10% of an undesired debromination product is obtained that has to be removed laboriously by repeated recrystallisation, the conversion of 3-bromo-5-methoxy-salicyl-aldehyde into brofaromine (A3-A8) is complicated and high in losses (yield 27.4% of the theoretical yield).

That can be attributed above all to the fact that the yield of the cyclocondensation step A3 cannot be increased beyond 45% of the theoretical yield. Moreover, in the hydrogenation of 1-methyl-4-(7-bromo-5-methoxy-benzofuran-2-yl)-1,2,5,6-tetrahydro-pyridine that follows and the subsequent demethylation of 1-methyl-4-(7-bromo-5-methoxy-benzo-furan-2-yl)piperidine (A6–A8), a product yield of only 64% of the theoretical yield is obtained.

The problem on which the invention was based was, therefore, to develop a process for the preparation of compounds of formula XII from 4-$R_4$O-phenol that completely or partly avoids the disadvantages of the known process.

This problem is solved by the process according to the invention which provides a route to the compounds of formula XII, especially brofaromine, which, in important steps or in its entirety, is novel and both ecologically and economically advantageous.

For example, starting from 5-bromosalicylaldehyde, by a combination of process steps b), c)+d) and f) and subsequent removal of the group —Y—$R_{10}$, shown below for brofaromine ($R_4$=methyl) in Scheme B1–B5, the product yield can already be more than doubled, from 27.4% of the theoretical yield to 62% of the theoretical yield (B1=91% of the theoretical yield; B2=89% of the theoretical yield; B3+B4= 86% of the theoretical yield; B5=89% of the theoretical yield).

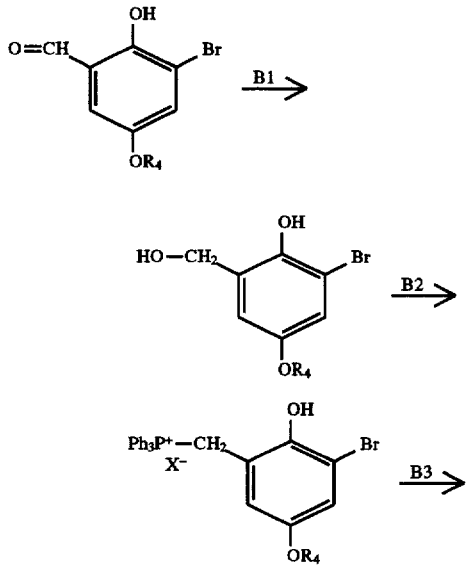

In particular, however, the process of the invention makes it possible, by a combination of process steps b), c)+d) and e) in accordance with Scheme C1–C3

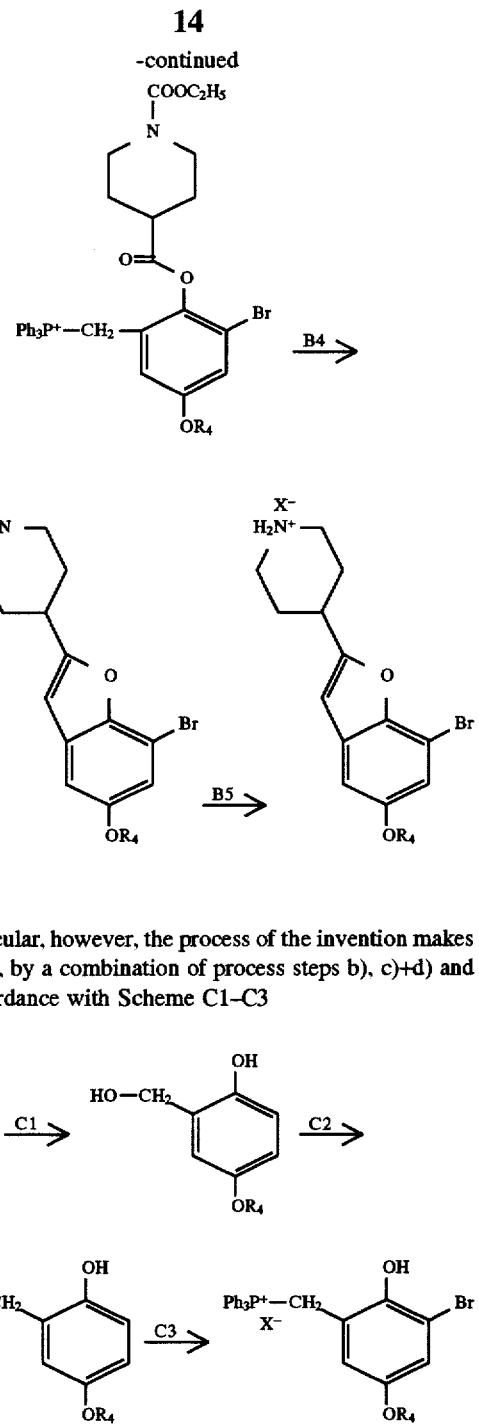

or by a combination of process steps a), b) and c)+d) in accordance with Scheme D1–D3

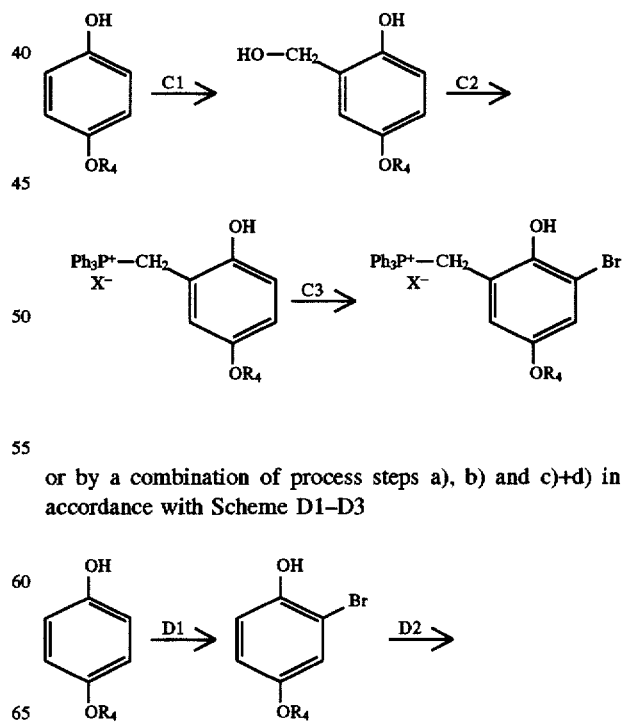

15
-continued

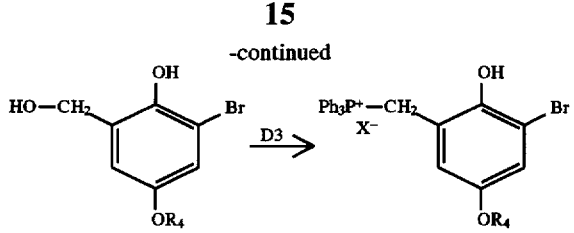 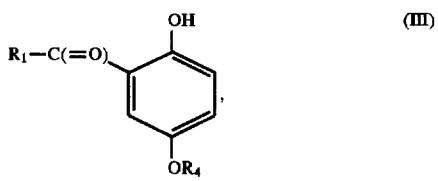

or by a combination of process steps a), b) and c)+d) in accordance with Scheme E1–E4

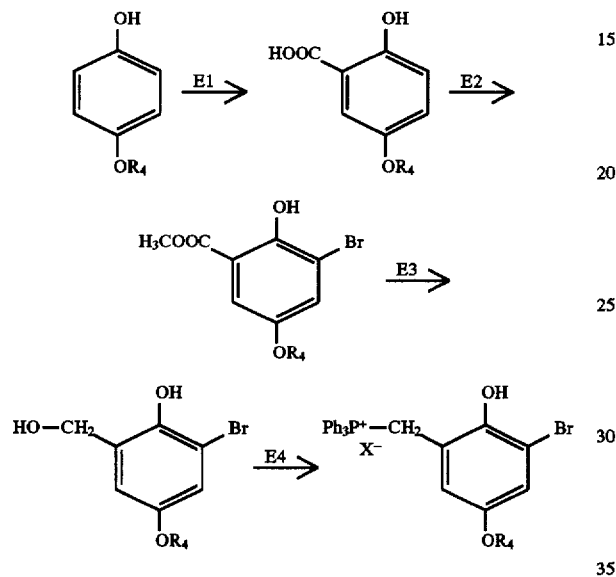

in the preparation of the (3-bromo-2-hydroxy-5-methoxybenzyl)phosphonium halide to avoid the high-loss circuitous route via the aldehyde steps and thus to increase the yield of 4.5% of the theoretical yield again to 37.9% of the theoretical yield (C1–C3), 41.8% of the theoretical yield (D1–D3) and 50.2% of the theoretical yield (E1–E4), respectively.

Using 4-methoxyphenol as starting material, it is easy according to the invention to achieve the following yields of brofaromine hydrochloride:

steps B1–B5:27.8%;
steps C1–C3, B3–B5:29.0%;
steps D1–D3, B3–B5:32.0% and
steps E1–E4, B3–B5:38.4%.

The invention accordingly also relates to a novel process for the preparation of compounds of the formula

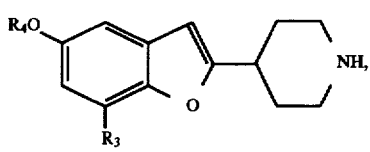
(XII)

wherein $R_3$ is halogen and $R_4$ is lower alkyl, and their salts, wherein

16 g) a compound of the formula

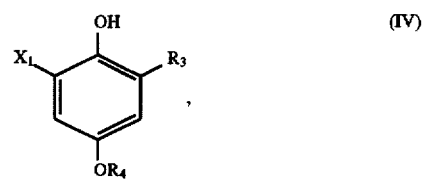
(III)

wherein $R_1$ is lower alkoxy and $R_4$ is lower alkyl, or a salt thereof, is halogenated in the m-position with respect to the carboxy group by treatment with elementary halogen in a lower alkanol, carboxy $R_1$—C(=O)—, where present, being esterified to form lower alkoxy-carbonyl, and in the resulting compound of the formula

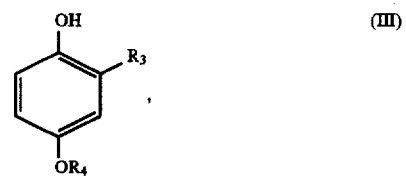
(IV)

wherein $X_1$ is lower alkoxycarbonyl, $R_3$ is halogen and $R_4$ is lower alkyl, or in a salt thereof, the group $X_1$ is reduced to hydroxymethyl, or a compound of the formula

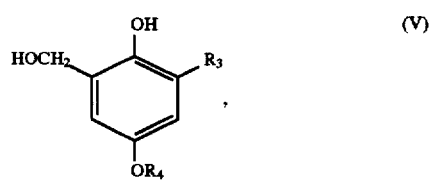
(III)

wherein $R_3$ is halogen and $R_4$ is lower alkyl, or a salt thereof, is reacted with paraform-aldehyde or trioxane and the resulting compound of the formula (V)

wherein $R_3$ is halogen and $R_4$ is lower alkyl, is reacted in the presence of a hydrohalic acid of the formula $HX_2$ with a compound of formula VIIc

(VIIc)

wherein each of $R_7$, $R_8$ and R9, independently of the others, is lower alkyl or unsubstituted or mono- or di-substituted phenyl or heteroaryl, wherein the substituents of the phenyl ring may be selected in each case from the group consisting of lower alkyl, lower alkoxy, nitro and halogen, or with the acid addition salt of a compound of formula VIIc and a hydrohalic acid of the formula $HX_2$, or a compound of the formula

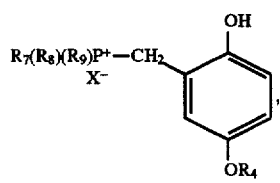

wherein $R_4$ is lower alkyl and wherein each of $R_7$, $R_8$ and $R_9$, independently of the others, is lower alkyl or unsubstituted or mono- or di-substituted phenyl or heteroaryl, wherein the substituents of the phenyl ring may be selected in each case from the group consisting of lower alkyl, lower alkoxy, nitro and halogen, is halogenated in the m-position with respect to the group of the formula $R_7(R_8)(R_9)P^+CH_2-$ by treatment with elementary halogen in a lower alkanol and in each case h) the resulting compound of the formula

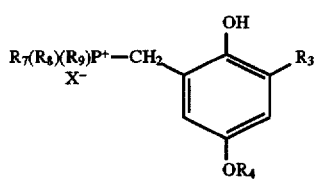

is reacted with a compound of the formula

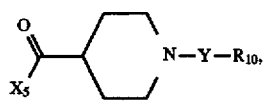

or with a salt thereof, wherein $X_5$ is halogen or a group of the formula $X_7-O-$, wherein $X_7$ denotes lower alkanesulfonyl, lower alkoxycarbonyloxy, or lower alkanoyl or a group of the formula

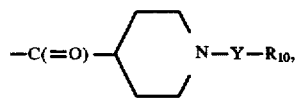

Y is a group of the formula $-(C=O)-$ (Ie) $R_{10}$ is lower alkoxy, lower alkenyloxy or benzyloxy, which is unsubstituted or mono- or di-substituted at the phenyl ring, wherein the substituents of the phenyl ring may be selected from the group consisting of lower alkyl, lower alkoxy, nitro and halogen, i) the resulting compound of the formula

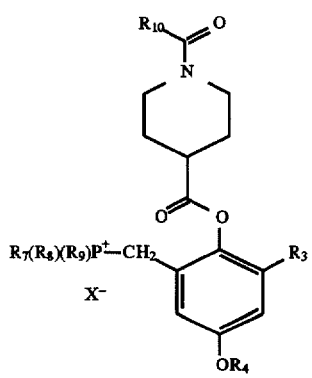

is cyclised to form the corresponding compound of the formula

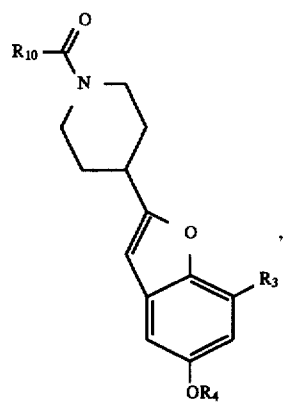

and j) the group of the formula $-C(=O)-R_{10}$ is removed from that compound, and if desired a resulting free compound is convened into an acid addition salt or a resulting acid addition salt is convened into the free compound or into a different acid addition salt.

The reactions of the process are carried out analogously to the methods of reacting and forming starting materials and intermediates of formulae III to IX, especially as described above under the process variants a) to f) resulting in compounds of formula I. In those reactions, even when not expressly mentioned below, the auxiliaries, such as the catalysts, the condensation agents and the solvolysis agents and/or the solvents and diluents, and the reaction conditions, such as the temperature and pressure conditions and, where appropriate, the protective gases, that are customary in each case are used.

In accordance with process variant g), the treatment of compounds of formulae III and XIII with halogen is effected, for example, as described above under process variants a) and e), respectively, the reduction of compounds of formula IV and the reaction of compounds of formula III with paraformaldehyde or trioxane is carried out, for example, as described above under process variant b) and the reaction of compounds of formulae Va and VIIc is carried out, for example, as described above under process variant d).

The reaction of compounds of formulae XIV and X in accordance with process variant h) is effected, for example, in a manner analogous to that indicated above for process variant f).

Cyclisation in accordance with process variant i) is effected, for example, in the presence of a basic condensation agent, such as an alkali metal carbonate, such as potassium carbonate, in an ester or a nitrile of a lower alkanoic acid, such as acetonitrile, advantageously with the phosphonium halide formed as secondary product being precipitated by the addition of an aliphatic hydrocarbon, such as a $C_5-C_{10}$alkane, for example hexane, to a solution of the crude product in an araliphatic hydrocarbon, such as toluene.

The removal of the group of the formula $-C(=O)-R_{10}$ in accordance with process variant i) can be carried out in customary manner, for example by treatment with a base, especially with potassium hydroxide in ethylene glycol.

The invention also relates to those embodiments of the processes described hereinbefore, according to which one starts from an intermediate obtainable at any stage of the process and executes the missing steps or in which a starting material is used in the form of a salt or, especially, is formed under the reaction conditions.

Novel starting materials which have been developed specifically for the manufacture of the compounds of the formula I according to the invention, as for example the novel compounds of the formula XV

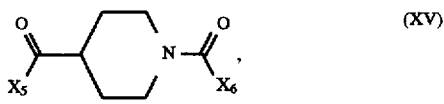

wherein $X_5$ is halogen or a group of the formula $X_7$—O—, wherein $X_7$ denotes lower alkanesulfonyl, lower alkoxycarbonyloxy, lower alkanoyl or a group of the formula

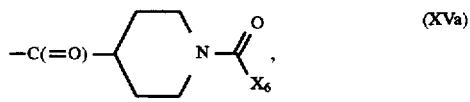

in which $X_6$ stands for lower alkoxy, lower alkenyloxy or phenyl-lower alkoxy which is unsubstituted or substituted by lower alkyl, lower alkoxy, nitro and/or halogen, and their salts, processes for their manufacture and their use as intermediates are also subject matters of the instant invention.

In compounds of the formula XV halogen denotes especially chloro or bromo, lower alkanesulfonyl is, for example, $C_1$–$C_4$-alkanesulfonyl, such as methane- or ethanesulfonyl, lower alkanoyl is, for example, $C_1$–$C_7$-alkanoyl, such as acetyl, propionyl, butyryl or pivaloyl, lower alkoxycarbonyl is, for example, $C_1$–$C_4$-alkoxycarbonyl, such as methoxycarbonyl, ethoxycarbonyl, propyloxycarbonyl, isopropyloxycarbonyl, butyloxycarbonyl, isobutyloxycarbonyl, sec.-butyloxycarbonyl or tert.-butyloxycarbonyl, lower alkoxy is, for example, $C_1$–$C_4$-alkoxy such as methoxy, ethoxy, propyloxy, isopropyloxy, buryloxy, isobutyloxy, sec.-butyloxy or ten.-butyloxy, lower alkenyloxy is especially allyloxy and phenyl-lower alkoxy is especially benzyloxy.

The invention relates, for example, to those compounds of the formula XV, wherein $X_5$ represents halogen or a group of the formula $X_7$—O— in which $X_7$ denotes lower alkanesulfonyl or lower alkoxycarbonyl and $X_6$ stands for lower alkoxy, and to their salts, to processes for their manufacture and to their use as intermediates.

The invention specifically relates to those compounds of the formula XV named in the examples, to processes for their manufacture and to their use as intermediates.

The process for the manufacture of the compounds of the formula XV is characterised in that a compound of the formula XVIII

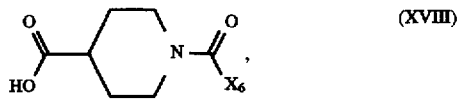

wherein $X_6$ has the meaning indicated hereinbefore, or a salt thereof is reacted with an agent capable of introducing the group $X_5$ and, if desired, a resulting compounds is convened into an other compound of the formula XV and/or a free compound obtainable according to the process is convened into a salt or a salt obtainable according to the process is convened into the free compound.

Agents capable of introducing a group $X_5$ are, for example, halogenating agents, such as halides of oxygen-containing acids of sulphur or phosphorus, such as thionyl chloride, thionyl bromide, phosphorus trichloride oder phosphorus pentachloride, or compounds of the formula $X_7$-$X_5$ (XIX), wherein $X_5$ and $X_7$ have the meanings given hereinbefore, such as corresponding lower alkanesulfonyl halides (XV; $X_7$=lower alkanesulfonyl, $X_5$=halo), lower alkanoic halides or lower alkanoic anhydrides (XV; $X_7$=lower alkanoyl, $X_5$=halo or —O$X_7$) or lower alkyl haloformates (XV; $X_7$=lower alkoxycarbonyl, $X_5$=halo).

The reaction is carried out according to known methods, for example, in the presence of of a basic condensation agent, such as a tertiary organic nitrogen base, such as pyridine, or an aliphatic or cycloaliphatic amine, for example in the presence of triethylamine, piperidine or N-methylmorpholine, advantageously in an araliphatic or halogen-aliphatic solvent, such as toluene or dichloromethane, at a temperature in the range of appropriately –25° C. to appropriately 50° C., for example of appropriately 0° C. to appropriately 25° C.

The Examples that follow serve to illustrate the invention; temperatures are even in degrees Celsius, pressures in mbar.

EXAMPLE 1

A suspension of 81.8 g of 2-bromo-4-methoxy-phenol and 24.9 g of boric acid in 55 ml of toluene is heated under reflux using a water separator until no further water separates off (approx. 12 hours). The thin light-brown suspension is then cooled to 90° and in the course of 40 minutes 13 g of paraformaldehyde are added in portions. The mixture is stirred for 1 hour at 90° and then cooled to 70°; 100 ml of water are added and the mixture is then cooled further to 20° and adjusted to pH 8.5 with concentrated sodium hydroxide solution. The brown suspension is stirred for 30 minutes and adjusted to pH 2.5 with concentrated sulfuric acid. The filter residue obtained after filtering with suction is washed twice with 50 ml of ethyl acetate each time. The combined filtrates are thoroughly mixed and the organic phase is separated off and concentrated by evaporation. The oily residue that remains is chromatographed on silica gel with toluene/ethyl acetate (4: 1) as eluant. The 3-bromo-2-hydroxy-5-methoxy-benzyl alcohol that is thus obtainable has an $R_f$ value of 0.3; yield 50% of the theoretical yield.

EXAMPLE 2

In the course of 1 hour, at from 5° to 10°, 18 g of sodium borohydride are added in portions to a solution of 160 g of 3-bromo-2-hydroxy-5-methoxy-benzaldehyde in 800 ml of ethanol. The resulting suspension is adjusted to pH 2.5 with sulfuric acid (10%) and the mixture is concentrated in vacuo to 500 ml. 200 ml of ethyl acetate are added thereto, the organic phase is separated off, the aqueous phase is extracted twice with 100 ml of ethyl acetate each time, and the combined organic phases are washed with water, dried over sodium sulfate and concentrated by evaporation. The oily residue that is obtained is crystallised from toluene to yield 3-bromo-2-hydroxy-5-methoxy-benzyl alcohol in the form of colourless crystals [m.p.: 76°; IR (KBr): 3500, 3280, 2930, 1580, 1470, 1425, 1285, 1235; 1190, 1165, 1125, 1060, 1050, 1040 $cm^{-1}$; $^1$H-NMR (360 MHz, $CDCl_3$), 2.40 (br. s, 1H, $CH_2OH$), 3.75 (s, 3H, $OCH_3$), 4.74 (s, 2H, $CH_2OH$), 6.34 (br. s, 1H, OH), 6.73 (d, 1H), 6.97 (d, 1H) ppm]; yield 91% of the theoretical yield.

EXAMPLE 3

In the course of 30 minutes, at from 40° to 60°, 67 g of hydrogen chloride are introduced into a solution of 459 g of triphenylphosphane and 387 g of 3-bromo-2-hydroxy-5-methoxy-benzyl alcohol in 600 ml of ethyl acetate. The reaction mixture is then stirred for 5 hours at 75°, the product beginning to crystallise after 30 minutes. The reaction mixture is cooled to 0° and stirred for a further one hour and then at that temperature the crystals are filtered off with suction. [(3-Bromo-2-hydroxy-5-methoxy-phenyl)-methyl]-triphenyl-phosphonium chloride is thus obtained in the form of colourless crystals [m.p.: 257° (decomposition); IR (KBr): 3010, 2880, 1605, 1585, 1565, 1440, 1420, 1330, 1260, 1225, 1150 cm$^{-1}$; $^1$H-NMR (360 MHz, CH$_3$OH-d$_4$); 3.50 (s, 3H, OCH$_3$), 4.84 (d, 2H, CH$_2$P$^+$), 6.49 (dd, 1H), 7.05 (dd, 1H), 7.61 to 7.77 (m, 12H), 7.88 (m, 3H) ppm]; yield 89% of the theoretical yield.

EXAMPLE 4

In the course of 1.5 hours, at 5°, 16 g of bromine are added dropwise to a solution of 50 g of [(2-hydroxy-5-methoxy-phenyl)methyl]-triphenyl-phosphonium bromide in 11 of methanol. The solution is then concentrated in vacuo at 20° to 130 ml, 250 ml of ethyl acetate are added thereto in the course of 2 hours, the resulting yellow suspension is stirred for 2 hours at 0°, and the slightly yellow crystals are filtered off with suction and recrystallised from methanol. [(3-Bromo-2-hydroxy-5-methoxy-phenyl)-methyl]-triphenyl-phosphonium bromide is thus obtained in the form of colourless crystals [m.p.: 259°; IR (KBr): 2875, 1585, 1565, 1415, 1325, 1200, 1165, 1150 cm$^{-1}$; $^1$H-NMR (360 MHz), DMSO-d$_6$); 3.43 (s, 3H, OCH$_3$), 5.03 (d, 2H, CH$_2$P$^+$), 6.42 (dd, 1H), 7.08 (dd, 1H, 7.61 to 7.80 (m, 12H), 7.92 (m, 3H), 9.00 (br, s, 1H, OH) ppm]; yield 76% of the theoretical yield

EXAMPLE 5

In the course of 30 minutes, at from 40° to 60°, 18 g of hydrogen chloride are introduced into a solution of 49.8 g of 2-hydroxy-5-methoxy-benzyl alcohol and 115.8 g of triphenylphosphane in 150 ml of acetonitrile. The reaction mixture is then stirred for 5 hours at 75°, the product beginning to crystallise after approx. 30 minutes. The reaction mixture is cooled to 0°, stirred for a further one hour and then at that temperature the crystals are filtered off with suction. [(2-Hydroxy-5-methoxy-phenyl)methyl]-triphenyl-phosphonium chloride is thus obtained in the form of colourless crystals [m.p.: 270° (decomposition); IR (KBr): 2990, 1585, 1395, 1295, 1240, 1145, 995 cm$^{-1}$; $^1$H-NMR (360 MHz, CH$_3$OH-d$_4$: 3.47 (s, 3H, OCH$_3$), 4.74 (d, 2H, CH$_2$P$^+$), 6.40 (dd, 1H), 6.62 (d, 1H), 6.73 (m, 1H), 7.56 to 7.72 (m, 12H), 7.87 (m, 3H) ppm]; yield 78% of the theoretical yield.

EXAMPLE 6

In the course of 1.5 hours, at 5°, 13 g of bromine are added dropwise to a solution of 35 g of [(2-hydroxy-5-methoxy-phenyl)methyl]-triphenyl-phosphonium chloride in 700 ml of methanol. The solution is concentrated in vacuo at 20° to 110 ml, 220 ml of ethyl acetate are added thereto in the course of 2 hours, the resulting yellow suspension is stirred for 2 hours at 0°, and the slightly yellow crystals are filtered off with suction and recrystallised from methanol. A mixture of colourless crystals (m.p.: 210°) which according to AgNO$_3$ titre comprises 22.4 percent by weight [(3-bromo-2-hydroxy-5-methoxy-phenyl)methyl ]-triphenyl-phosphonium chloride and 77.6 percent by weight [(3-bromo-2-hydroxy-5-methoxy-phenyl)methyl]-triphenyl-phosphonium bromide is obtained; yield 76 % of the theoretical yield.

EXAMPLE 7

With the exclusion of air, 43.9 g of 4-chlorocarbonyl-1-ethoxycarbonyl-piperidine are dissolved in 250 ml of anhydrous acetonitrile (degassed) and 53.4 g of [(3-bromo-2-hydroxy-5-methoxy-phenyl)methyl]-triphenyl-phosphonium chloride are added to the solution. In the course of 30 minutes, at 25° to 30°, 20 g of pyridine are added dropwise to the resulting suspension. The mixture is heated for 5 hours under reflux and is then hydrolysed with 100 ml of sodium carbonate solution (15%); the organic phase is separated off, washed in succession with 100 ml of 1N hydrochloric acid and 100 ml of water and concentrated by evaporation in vacuo and the oily residue that remains is dissolved in 50 ml of dichloromethane. In the course of 30 minutes, at 20°, with vigorous stirring, 200 ml of ethyl acetate are added dropwise to that solution and the product crystallises out. The resulting crystal suspension is concentrated to 150 ml under a weak vacuum using a rotary evaporator and then stirred for 2 hours at 0°. Filtering with suction and drying yield [(3-bromo-2-[(1-ethoxycarbonylpiperid-4-yl)carbonyloxy]-5-methoxy-phenyl)methyl ]-triphenyl-phosphonium chloride [m.p.: 196°; IR (KBr): 3415, 3060, 2855, 2780, 1600, 1565, 1385, 1270, 1190, 1165 cm$^{-1}$; $^1$H-NMR (360 MHz, CDCl$_3$); 1.28 (t, 3H, CO$_2$CH$_2$CH$_3$), 1.45 (m, 2H), 1.75 (m, 2H), 2.58 (m, 1H), 2.87 (m, 2H), 2.47 (s, 3H, OCH$_3$), 4.00 (m, 2H), 4.13 (q, 2H, CO$_2$CH$_2$CH$_3$), 5.37 (br, d, 2H, CH$_2$P$^+$), (dd, 1H), 7.07 (dd, 1H), 7.54 to 7.87 (m, 15H) ppm]; yield 66% of the theoretical yield.

EXAMPLE 8

First 1.0 g of N,N-dimethylformamide and then, in the course of 2 hours, at 68° to 70°, 369.0 g of thionyl chloride are added to a solution of 578.2 g of 4-carboxy-1-ethoxycarbonyl-piperidine in 1200 ml of toluene. The reaction mixture is stirred for 30 minutes at 70°, and the toluene is then distilled off in vacuo and the residue is then degassed for approx. 30 minutes at room temperature under a high vacuum. 4-Chlorocarbonyl-1-ethoxycarbonyl-piperidine is thus obtained in the form of a slightly yellow oil [content of product according to NaOH and AgNO$_3$ titre: 98%; IR (film): 2960, 2870, 1790, 1695, 1470, 1435, 1300, 1230, 1130, 960, 765 cm$^{-1}$]. The product distils, without decomposition, at b.p. =96°–98° (0.08–0.09 torr); distillation yield 94.7% of the theoretical yield.

EXAMPLE 9

In an analogous manner as described in Example 7 4-chlorocarbonyl-1-benzyloxycarbonyl-piperidine is obtained starting from 4-carboxy-1-ethoxycarbonyl-piperidine.

EXAMPLE 10

In an analogous manner as described in Example 8, 4-chlorocarbonyl-1-allyloxycarbonyl-piperidine is obtained starting from 4-carboxy-1-allyloxycarbonyl-piperidine.

EXAMPLE 11

In a three-neck flask, 24.1 g (0.12 mol) of 4-carboxy-1-ethoxycarbonyl-piperidine are dissolved in 150 ml of toluene. After cooling to 0°, 13.8 g (0.120 mol) of methanesulfonyl chloride are added to the stirred solution dropwise over a period of 5 minutes. Then a solution of 12.1 g (0.12 mol) of N-methylmorpholine in 50 ml of toluene is added dropwise over a period of 15 minutes. The reaction mixture is stirred for additional 30 minutes at 20°. Then the N-methylmorpholine-hydrochloride formed is filtered off. The resulting yellowish solution of 4-ethoxycarbonyl-1- methanesulfonyloxy-carbonyl-piperidine can be used in the next reaction step without further purification.

EXAMPLE 12

In an analogous manner as described in Example 11, 1-ethoxycarbonyl-4-pivaloyloxycarbonyl-piperidine can be obtained reacting 4-carboxy-1-ethoxycarbonyl-piperidine with pivaloyl chloride.

EXAMPLE 13

In a dried three-neck flask, 27.7 g (0.138 mol) of 4-carboxy-1-ethoxy-carbonyl-piperidine are dissolved in 120 ml of dichloromethane. After cooling to −10°, a solution of 18.48 g (0.138 mol) of isobutyl chloroformate (chloroformic acid isobutyl ester) in 15 ml of dichloromethane are added dropwise to the stirred solution over a period of 5 minutes.

After stirring at −10° for additional 5 minutes, a solution of 13.98 g (0.138 mol) of triethylamine in 15 ml of dichloromethane is added dropwise over a period of 15 minutes. The reaction mixture is stirred for additional 30 minutes at 0°. The clear, light-yellowish solution of 4-ethoxycarbonyl-1-isobutyloxycarbonyl-piperidine can be used in the next reaction step without further purification.

In order to avoid forming of solvent mixtures in the next reaction step (cf. Example 18), the dichloromethane may be removed by distillation under reduced pressure and exclusion of moisture and the oily residue may be redissolved in anhydrous acetonitrile.

EXAMPLE 14

In an analogous manner as described in Examples 8, 11 and 13, 1,1'-bis(ethoxycarbonyl)piperidine-4-carboxylic acid anhydride may be obtained reacting 4-carboxy-1-ethoxycarbonyl-piperidine with 4-chlorocarbonyl-1-ethoxycarbonyl-piperidine.

EXAMPLE 15

In the course of 30 minutes, at room temperature, 20 g of hydrogen bromide are introduced into a suspension of 50 g of 3-bromo-2-hydroxy-5-methoxy-benzyl alcohol in 300 ml of anhydrous acetic acid. The reaction mixture is stirred for 5 hours at room temperature and the resulting solution is concentrated by evaporation. The black-brown oily residue, which crystallises slowly when left to stand at room temperature, is crystallised from ethyl acetate/cyclohexane (5:1) with the addition of a small amount of activated charcoal. 3-Bromo-2-hydroxy-5-methoxy-benzyl bromide is thus obtained [$^1$H-NMR (360 MHz, CDCl$_3$); 3.75 (s, 3H, OCH$_3$), 4.53 (s, 2H, CH$_2$BR), 5.45 (s, 1H, OH), 6.85 (d, 1H), 7.00 (d, 1H) ppm].

EXAMPLE 16

8.8 g of trimethyl phosphite are added to 20.0 g of 3-bromo-2-hydroxy-5-methoxy-benzyl bromide and, with stirring, the mixture is heated for 3 hours at 140° (complete conversion according to TLC). The resulting oil is filtered with toluene/ethyl acetate (4:1) as eluant over a small amount of silica gel. [(3-Bromo-2-hydroxy-5-methoxy-phenyl)methyl ]phosphonic acid dimethyl ester is thus obtained [$^1$H-NMR (360 MHz, CDCl$_3$); 3.20 (d, 2H, CH$_2$P, $^2J_{P-H}$=21 Hz), 3.70 (s, 3H, OCH$_3$), 3.74 (d, 6H, 2×OCH$_3$, $^3J_{P-H}$=1 Hz), 6.70 (m, 1H), 7.07 (m, 1H) ppm].

EXAMPLE 17

In the course of 30 minutes, at 25° to 30°, with the exclusion of air, 50 g of [(3-bromo-2-[(1-ethoxycarbonylpiperid4-yl)carbonyloxy]-5-methoxyphenyl)methyl]-triphenyl-phosphonium chloride are introduced into a suspension of 20 g of ground potassium carbonate (anhydrous) in 100 ml of acetonitrile. The mixture is stirred for 2 hours at room temperature, then 80 ml of water are added thereto, and the mixture is acidified to pH 1.0 with concentrated hydrochloric acid. The organic phase is separated off and concentrated by evaporation. The oily residue is taken up in 50 ml of toluene and at 20°, in the course of 1 hour, 100 ml of hexane are added; the major portion (approx. 90%; content according to HPLC: 90%) of the triphenylphosphane oxide that forms crystallises out. The crystal suspension is filtered with suction and the filter cake is washed twice with 40 ml of hexane/toluene (3:2) each time. Concentration of the combined filtrates by evaporation and chromatography of the residue on silica gel with toluene/ethyl acetate (2:1) as eluant yield 4-(7-bromo-5-methoxy-benzofuran-2-yl)- 1-ethoxycarbonyl-piperidine [m.p.: 85°; $^1$H-NMR (360 MHz, CDCl$_3$); 1.28 (t, 3H, CO$_2$CH$_2$CH$_3$), 1.69 (m, 2H), 2.09 (m, 2H), 2.95 (m, 3H), 3.80 (s, 3H, OCH$_3$), 4.16 (q, 2H, CO$_2$CH$_2$CH$_3$), 4.14 to 4.35 (br. m, 2H), 6.36 (s, 1H), 6.90 (d, 1H), 7.00 (d, 1H) ppm]; yield 90% of the theoretical yield.

EXAMPLE 18

In the course of from 1.5 to 2 hours, at from 25° to 30°, with the exclusion of air, 49 g of 4-chlorocarbonyl-1-ethoxycarbonyl-piperidine are added dropwise to a suspension of 105 g of [(3-bromo-2-hydroxy-5-methoxyphenyl)methyl]-triphenyl-phosphonium chloride and 115 g of ground potassium carbonate (anhydrous) in 250 ml of acetonitrile. The reaction mixture is stirred for 30 minutes at from 25° to 30°, then 350 ml of water are added and the resulting mixture is acidified to pH 1.0 with concentrated hydrochloric acid. The organic phase is separated off and concentrated by evaporation. The oily residue is taken up in 160 ml of toluene and in the course of 1 hour, at 20°, 250 ml of hexane are added, and the major portion (approx. 80%; content according to HPLC: 85%) of the triphenylphosphane oxide that forms crystallises out. The crystal suspension is filtered with suction and the filter cake is washed twice with 40 ml of hexane/toluene (3:2) each time. The combined filtrates are concentrated by evaporation and the oily residue is chromatographed on silica gel with toluene/ethyl acetate (2:1) as eluant. 4-(7-Bromo-5-methoxy-benzofuran-2-yl)-1-ethoxycarbonyl-piperidine, which is identical to the product obtainable according to Example 10, is thus obtained; yield 86% of the theoretical yield.

EXAMPLE 19

In the course of from 30 to 45 minutes, at 20°, with stirring, 43.9 g of bromine are added dropwise to a solution of 45.9 g of 2-hydroxy-5-methoxy-benzoic acid methyl ester in 125 ml of heptane. The reaction mixture is then stirred for a further 3 to 4 hours, then diluted with 110 ml of water and stirred for a further one hour and then 295 ml of heptane and 46 ml of tert-butyl methyl ether are added thereto. The mixture is then heated to from 50° to 55° and the aqueous phase is separated off. The organic phase is extracted twice with 114 ml of water each time and cooled to −20°. The crystals which precipitate are filtered off and dried under a high vacuum. 3-Bromo-2-hydroxy-5-methoxy-benzoic acid methyl ester is thus obtained; yield 82.5% of the theoretical yield.

EXAMPLE 20

In the course of 1 hour, at 20°, with stirring, a solution of 57 g of 3-bromo-2-hydroxy-5-methoxy-benzoic acid methyl ester in 110 ml of tetrahydrofuran are added dropwise to a solution of 8 g of sodium borohydride in 280 ml of tetrahydrofuran. The reaction mixture is stirred for a further 2.5 hours, hydrolysed with 105 ml of 2N hydrochloric acid and adjusted to pH 2.5. The aqueous phase is separated off. The organic phase is extracted three times with 90 ml of sodium chloride solution (10%) each time, concentrated by evaporation using a rotary evaporator, diluted with 100 ml of toluene, concentrated to 100 g using a rotary evaporator and in the course of 30 minutes, at 60°, added to a suspension, heated to from 70° to 80°, of 55.1 g of triphenylphosphane, 8.8 g of hydrogen chloride and 42 ml of toluene. The reaction mixture is stirred for a further 7 hours and then cooled to from 0° to −5°. The crystals that have formed are filtered off, washed four times with 40 ml of toluene each time and dried under a high vacuum. [(3-Bromo-2-hydroxy-5-methoxy-phenyl)methyl]-triphenyl-phosphonium chloride, which is identical to the product obtainable according to Example 3, is obtained; yield 79% of the theoretical yield.

EXAMPLE 21

7.6 g of 4-(7-bromo-5-methoxy-benzofuran-2-yl)-1-ethoxycarbonyl-piperidine are dissolved in 80 ml of ethylene glycol. After the addition of 19.4 g of 86% potassium hydroxide, the resulting cloudy solution is heated at 160° with vigorous stirring for 18 hours. The reaction mixture is cooled to 100°, diluted with 80 ml of toluene, and cooled further to 20°. The reaction solution is extracted twice with 1000 ml of water each time and then four times with 200 ml of a 10% solution of methanesulfonic acid in water each time. The resulting solution in methanesulfonic acid is adjusted to pH 12 by the addition of 30% sodium hydroxide solution and extracted by shaking with 1000 ml of chloroform. The chloroform solution is dried over sodium sulfate, filtered and concentrated by evaporation. Crystallisation from ethyl acetate yields 4-(7-bromo-5-methoxy-benzofuran-2-yl)-piperidine having a melting point of 149°–152°. There is obtained from the base by treatment with methanolic hydrochloric acid and recrystallisation from methanol/ether 4-(7-bromo-5-methoxy-benzofuran-2-yl)-piperidine-hydrochloride having a melting point of 242°–243°.

What is claimed is:

1. A compound of formula I

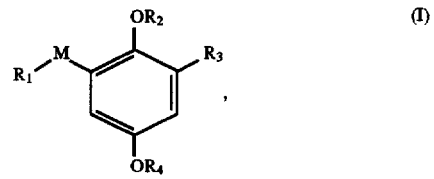

wherein $R_4$ is lower alkyl and $R_1$ is —$P^+(R_7)(R_8)R_9 X^-$ (Ib), M is methylene $R_2$ is a group of the formula

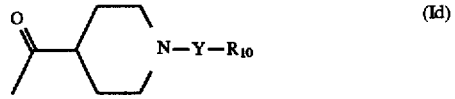

and $R_3$ is hydrogen or halogen, or, M is carbonyl, and $R_3$ is halogen, each of $R_7$, $R_8$ and $R_9$, independently of the others, is lower alkyl, unsubstituted or mono- or di-substituted phenyl, wherein the substituents of the phenyl ring may be selected in each case from the group consisting of lower alkyl, lower alkoxy, nitro and halogen, or is furyl, $X^-$ is the anion of a hydrohalic acid, a lower alkanesulfonic acid, a halo-lower alkanesulfonic acid or of a benzenesulfonic acid that is unsubstituted or mono-substituted by lower alkyl or by halogen, and wherein either Y is a direct bond and $R_{10}$ is lower alkyl, allyl, cyano, lower alkanesulfonyl, halo-lower alkanesulfonyl, benzyl that is unsubstituted or mono- or di-substituted at the phenyl ring, wherein the substituents of the phenyl ring may be selected from the group consisting of lower alkyl, lower alkoxy, nitro and halogen, or is benzenesulfonyl that is unsubstituted or mono-substituted by lower alkyl or by halogen, or Y is a group of the formula —(C=O)— (Ie) or a group of the formula —(C=S)— (If) and $R_{10}$ is halogen, lower alkyl, halo-lower alkyl, lower alkoxy, lower alkenyloxy, phenyl-lower alkenyloxy, halo-lower alkoxy or lower alkylthio, or is phenyl, phenoxy, phenylthio, benzyl, benzyloxy or benzylthio, each of which is unsubstituted or mono- or di-substituted at the phenyl ring, wherein the substituents of the phenyl ring may be selected in each case from the group consisting of lower alkyl, lower alkoxy, nitro and halogen, with the proviso that, in a compound I wherein $R_1$ is a group Ib wherein each of $R_7$, $R_8$ and $R_9$ is unsubstituted phenyl and $X^-$ is the bromide ion, M is methylene, and $R_4$ is methyl, $R_3$ is other than hydrogen.

2. A compound according to claim 1 being [(3-bromo-2-[(1-ethoxycarbonytpiperid-4-yl)-carbonyloxy]-5-methoxy-phenyl)methyl]-triphenyl-phosphonium chloride.

* * * * *